(12) United States Patent
Boden et al.

(10) Patent No.: US 8,734,500 B2
(45) Date of Patent: May 27, 2014

(54) DISTAL DETACHMENT MECHANISMS FOR VASCULAR DEVICES

(75) Inventors: Thomas Boden, Raynham, MA (US);
Michael C. Brown, Raynham, MA (US)

(73) Assignee: Depuy Synthes Products, LLC, Raynham, MA (US)

( * ) Notice: Subject to any disclaimer, the term of this patent is extended or adjusted under 35 U.S.C. 154(b) by 160 days.

(21) Appl. No.: 13/246,343

(22) Filed: Sep. 27, 2011

(65) Prior Publication Data

US 2013/0079864 A1  Mar. 28, 2013

(51) Int. Cl.
*A61F 2/82* (2013.01)

(52) U.S. Cl.
USPC ........................................................ 623/1.12

(58) Field of Classification Search
USPC ............... 606/108; 623/1.11, 1.12, 1.23, 1.34
See application file for complete search history.

(56) References Cited

U.S. PATENT DOCUMENTS

| | | | | |
|---|---|---|---|---|
| 5,534,007 A * | 7/1996 | St. Germain et al. | ......... | 623/1.11 |
| 5,662,622 A | 9/1997 | Gore | | |
| 5,702,418 A * | 12/1997 | Ravenscroft | ................. | 623/1.11 |
| 5,972,019 A | 10/1999 | Engelson | | |
| 6,063,100 A | 5/2000 | Diaz | | |
| 6,077,295 A * | 6/2000 | Limon et al. | ................. | 623/1.11 |
| 6,179,857 B1 | 1/2001 | Diaz | | |
| 6,254,609 B1* | 7/2001 | Vrba et al. | .................... | 606/108 |
| 6,346,118 B1* | 2/2002 | Baker et al. | ................... | 623/1.12 |
| 6,398,802 B1* | 6/2002 | Yee | ............................. | 623/1.13 |
| 6,517,569 B2 | 2/2003 | Mikus | | |
| 6,645,240 B2* | 11/2003 | Yee | .............................. | 623/1.11 |
| 7,175,650 B2* | 2/2007 | Ruetsch | ....................... | 623/1.12 |
| 7,309,352 B2 | 12/2007 | Eder | | |
| 7,329,275 B2* | 2/2008 | Yee | .............................. | 623/1.11 |
| 7,351,255 B2 | 4/2008 | Andreas | | |
| 7,485,122 B2 | 2/2009 | Teoh | | |
| 7,517,361 B1* | 4/2009 | Ravenscroft | ................. | 623/1.12 |
| 7,632,298 B2* | 12/2009 | Hijlkema et al. | ............ | 623/1.12 |
| 7,674,282 B2 | 3/2010 | Wu | | |
| 7,942,924 B1* | 5/2011 | Perez et al. | ................... | 623/1.23 |
| 2001/0007082 A1* | 7/2001 | Dusbabek et al. | ........... | 623/1.11 |
| 2002/0055767 A1 | 5/2002 | Forde | | |
| 2002/0120323 A1* | 8/2002 | Thompson et al. | .......... | 623/1.11 |

(Continued)

FOREIGN PATENT DOCUMENTS

| | | |
|---|---|---|
| EP | 1000590 A1 | 5/2000 |
| EP | 1440673 A1 | 7/2004 |
| WO | WO 2011094527 A1 | 8/2011 |

OTHER PUBLICATIONS

Codman Neurovascular—Codman Enterprise™ VRD Brochure; 2009; pp. 1-8; Codman & Shutleff, Inc., Raynham, MA.

(Continued)

*Primary Examiner* — Ryan Severson

(57) ABSTRACT

A system for delivering an expandable implant into the vasculature of a patient, including an elongated core element having a proximal end accessible exterior to the patient and a distal end including at least one feature for engaging a proximal portion of the implant in a collapsed state. The system further includes an expansion limiter having an inner diameter and a length sufficient to cover the proximal portion of the implant and to retain the proximal portion in the collapsed state, and at least one elongated member having a distal end connected to the expansion limiter and a proximal end accessible exterior to the patient to enable proximal movement of the expansion limiter to release the implant.

12 Claims, 6 Drawing Sheets

(56) References Cited

U.S. PATENT DOCUMENTS

| | | | |
|---|---|---|---|
| 2002/0193862 A1* | 12/2002 | Mitelberg et al. | 623/1.2 |
| 2003/0216807 A1* | 11/2003 | Jones et al. | 623/1.22 |
| 2003/0233140 A1* | 12/2003 | Hartley et al. | 623/1.11 |
| 2004/0006380 A1* | 1/2004 | Buck et al. | 623/1.11 |
| 2004/0087900 A1 | 5/2004 | Thompson | |
| 2007/0260301 A1 | 11/2007 | Chuter | |
| 2007/0260302 A1* | 11/2007 | Igaki | 623/1.12 |
| 2008/0082158 A1* | 4/2008 | Tseng et al. | 623/1.13 |
| 2008/0288043 A1* | 11/2008 | Kaufmann et al. | 623/1.11 |
| 2009/0125093 A1* | 5/2009 | Hansen | 623/1.11 |
| 2009/0138065 A1* | 5/2009 | Zhang et al. | 623/1.12 |
| 2009/0287292 A1* | 11/2009 | Becking et al. | 623/1.11 |
| 2010/0057185 A1* | 3/2010 | Melsheimer et al. | 623/1.12 |
| 2010/0063573 A1* | 3/2010 | Hijlkema et al. | 623/1.11 |
| 2011/0125244 A1 | 5/2011 | Roeder | |

OTHER PUBLICATIONS ev3 Neurovascular—Solitaire™ AB Neurovascular Remodeling Device Brochure; 2009; pp. 1-6; Micro Therapeutics, Inc., d/b/a ev3 Neurovascular, Irvine CA.

* cited by examiner

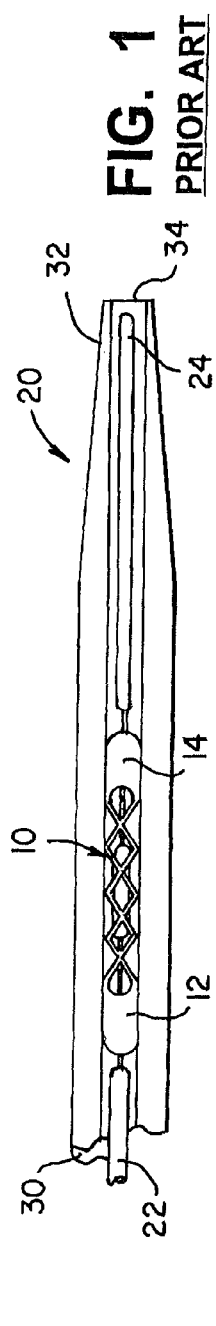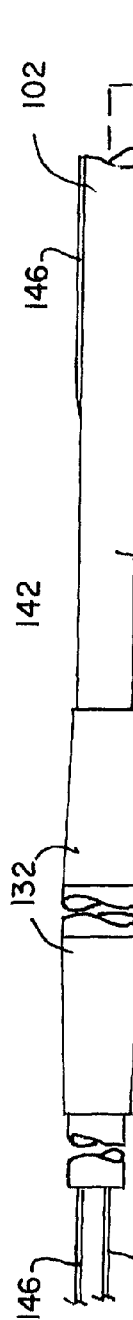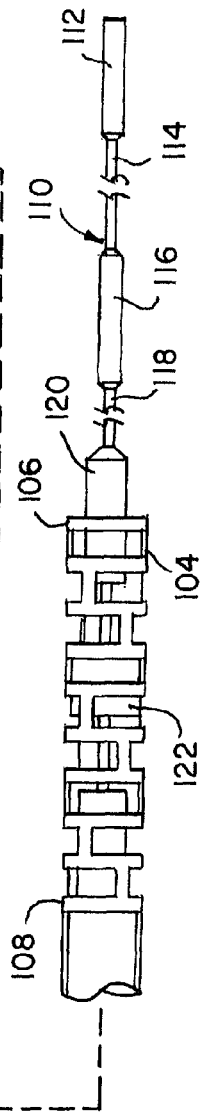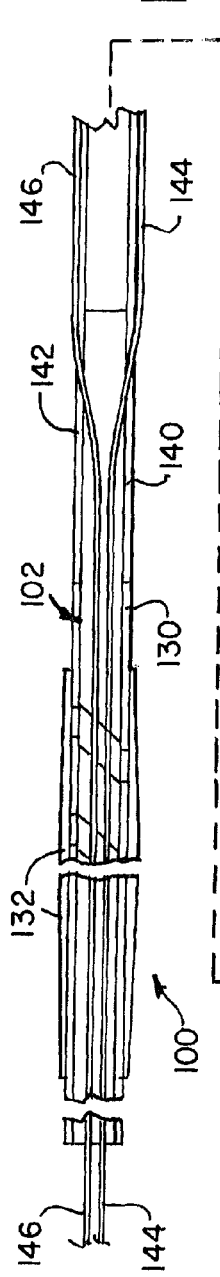
FIG. 1 PRIOR ART
FIG. 2
FIG. 3

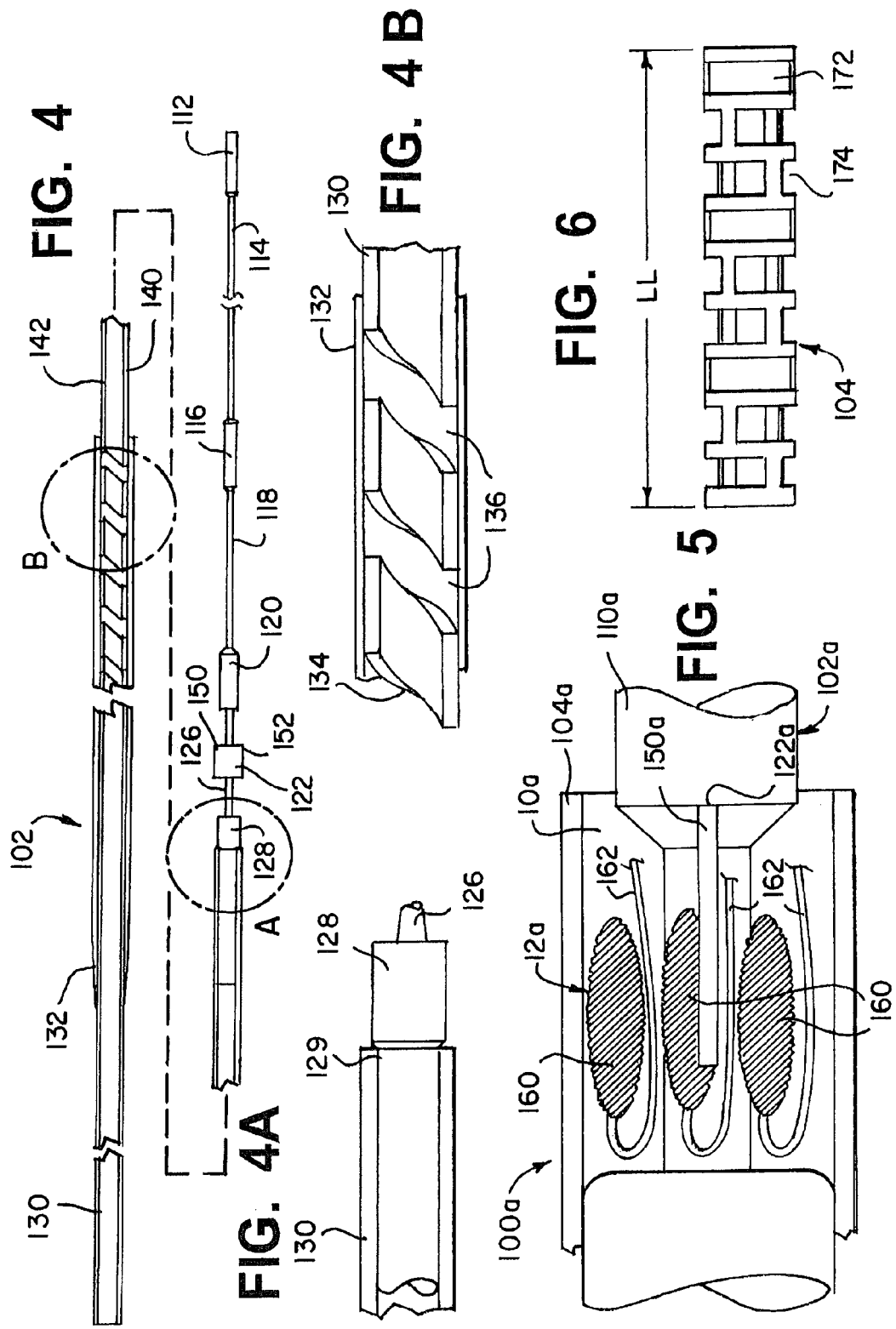

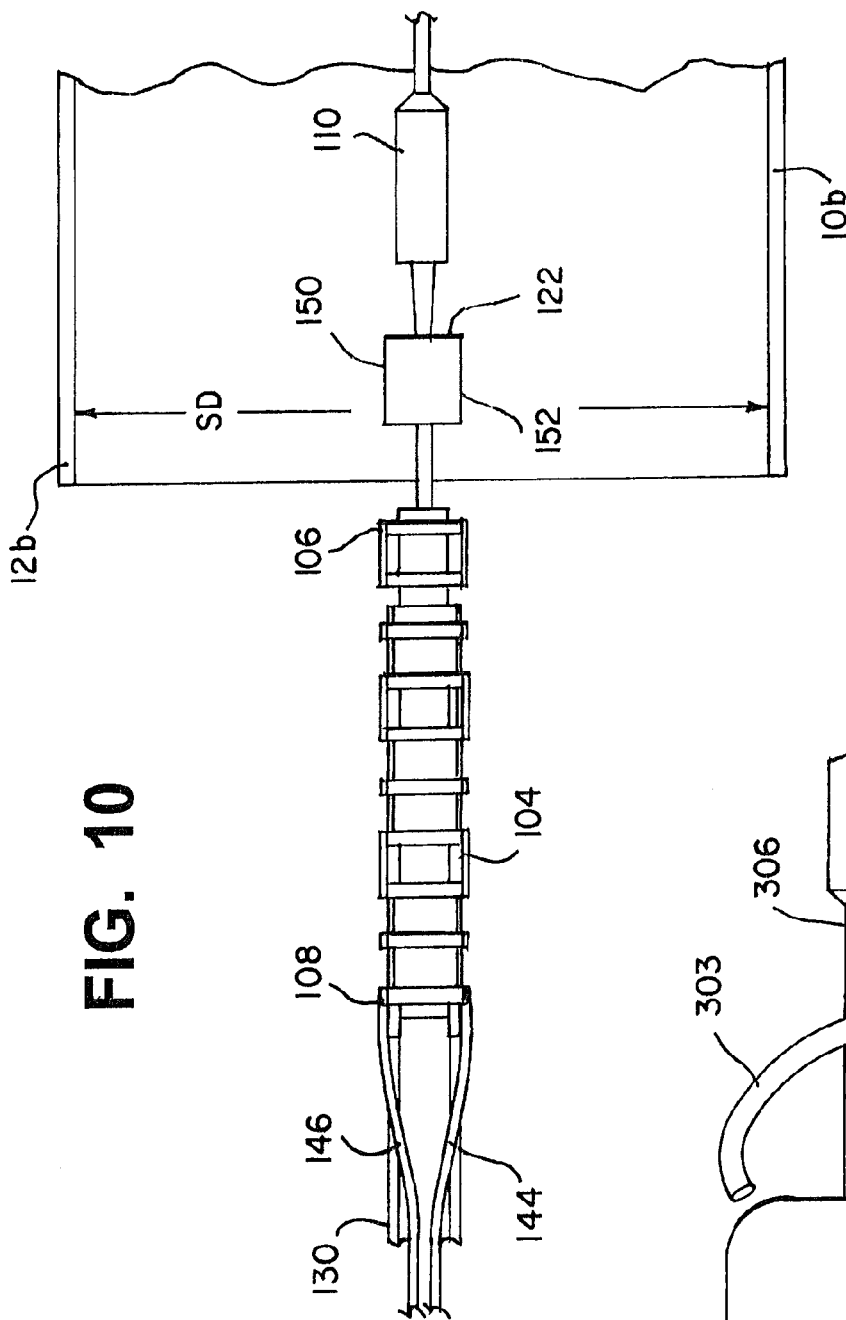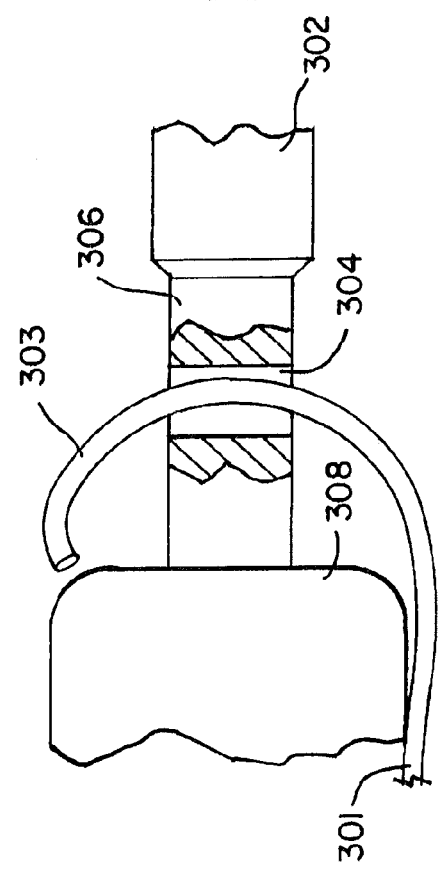

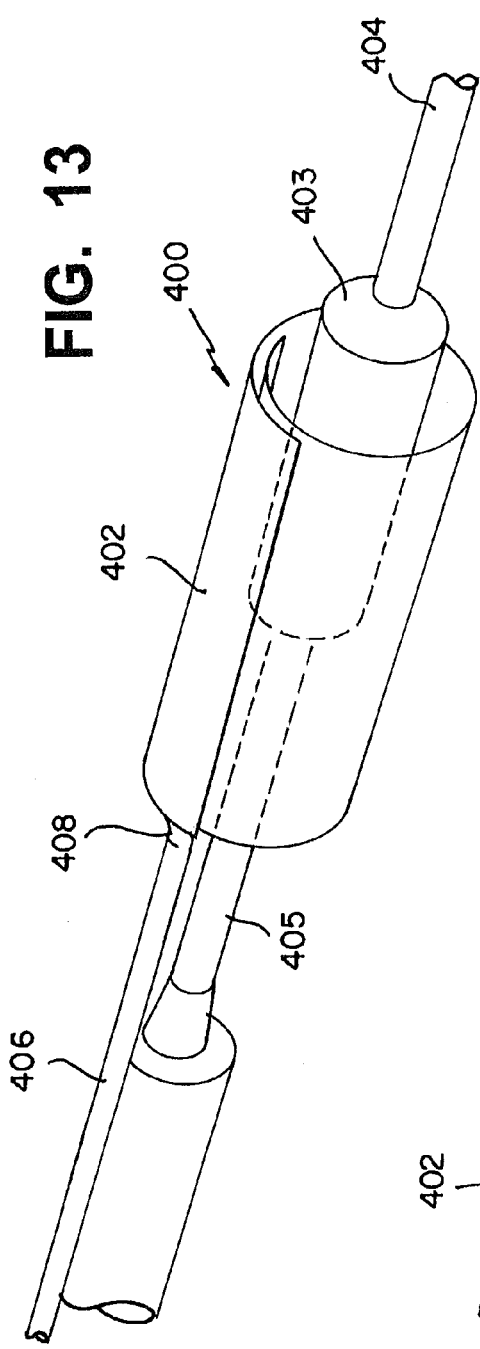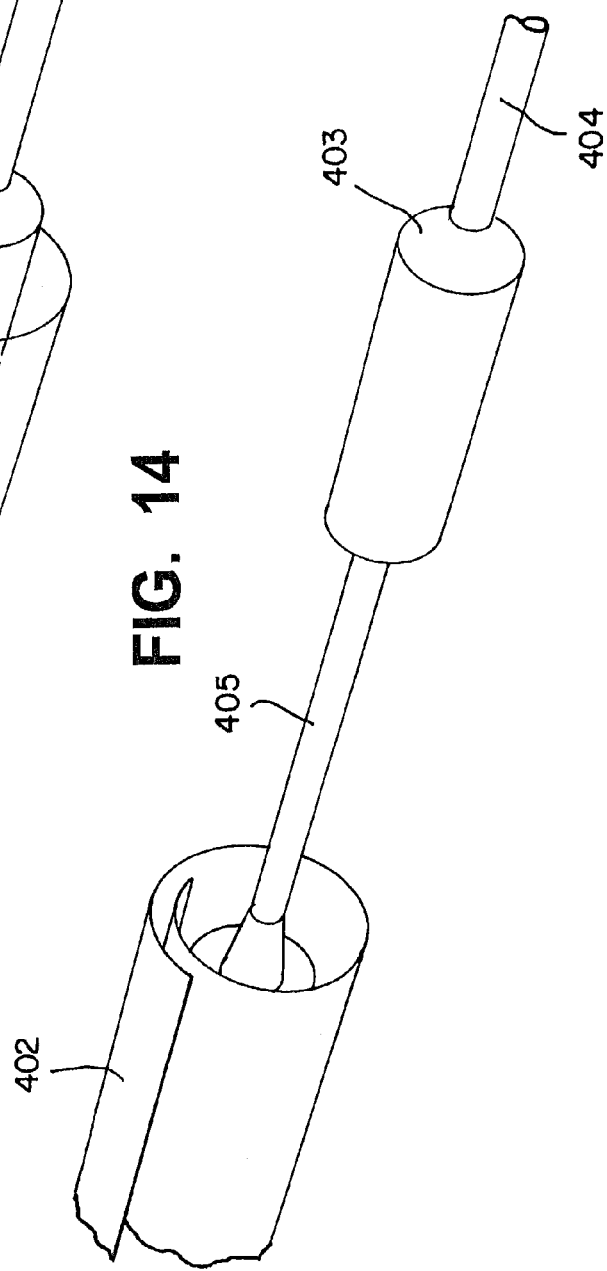

DISTAL DETACHMENT MECHANISMS FOR VASCULAR DEVICES

BACKGROUND OF THE INVENTION

1. Field of the Invention

The invention relates to the delivery of implants within body vessels and more particularly to mechanisms for selectively releasing stents and other expandable vascular implants.

2. Description of the Related Art

Vascular disorders and defects such as aneurysms, embolisms, and other arteriovenous malformations are especially difficult to treat when located near critical tissues or where ready access to a malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

Alternative treatments include vascular occlusion devices such as stents and embolic coils deployed using delivery catheters having a distal end positioned at an occlusion or aneurysm. Several types of stent delivery systems are disclosed in U.S. Patent Publication No. 2005/0049670 by Jones et al., for example.

In a currently preferred procedure to treat a cranial aneurysm, the distal end of an embolic coil delivery catheter is inserted into non-cranial vasculature of a patient, typically through a femoral artery in the groin, and guided to a predetermined delivery site within the cranium. A number of delivery techniques for vaso-occlusive devices, including use of fluid pressure to release an embolic coil once it is properly positioned, are described for example by Diaz et al. in U.S. Pat. Nos. 6,063,100 and 6,179,857.

Often, before embolic coils are implanted, a stent-like vascular reconstruction device is first guided beneath the aneurysm using a delivery catheter. One commercially available reconstruction product is the CODMAN ENTERPRISE® Vascular Reconstruction Device and System as described, for example, in a Navigate Tough Anatomy brochure Copyright 2009 by Codman & Shurtleff, Inc., 325 Paramount Drive, Raynham, Mass. The CODMAN ENTERPRISE® device is carried by a central delivery wire and initially held in place on the delivery wire in a collapsed state by a sheath-type introducer. Typically, a delivery catheter such as a PROWLER® SELECT® Plus microcatheter, also commercially available from Codman & Shurtleff and as disclosed by Gore et al. in U.S. Pat. No. 5,662,622, for example, is first positioned intravascularly with its distal tip slightly beyond the neck of the aneurysm. The tapered distal tip of the introducer is mated with the proximal hub of the delivery catheter, and the delivery wire is then advanced through the delivery catheter.

The CODMAN ENTERPRISE® device has a highly flexible, self-expanding closed cell design with a number of radiopaque markers at each flared end of the device, similar to the stent illustrated in the published patent application by Jones et al., cited above. After the device is properly positioned and allowed to expand against the parent vessel, one or more embolic coil delivery catheters can be threaded through one of the cells of the expanded device and then into the aneurysm to place embolic coils therein.

The CODMAN ENTERPRISE® device can be partially deployed and recaptured once by carefully manipulating the delivery catheter relative to the central delivery wire to allow the distal portion of the device to expand while retaining the distal tip of the delivery catheter over the proximal portion of the device. This action continues to trap the radiopaque markers at the proximal end of the device within an indentation formed in the delivery wire. However, if the delivery catheter is withdrawn even slightly past the indentation, the CODMAN ENTERPRISE® device will become fully expanded and cannot be recaptured or repositioned by the delivery system.

A number of well-known stent delivery systems, for both self-expanding and mechanically expanding stents, are described by Ravenscroft in U.S. Pat. No. 5,702,418, for example. Partial deployment and retraction of a stent is identified as an important criterion to enable a physician to recover a stent that is not initially deployed in a proper position.

A delivery system having a weak, non-marring inner sheath and a stronger outer sheath is disclosed by Vrba et al. in U.S. Pat. No. 6,254,609. Another delivery system utilizing inner and outer sheaths is disclosed by Ruetsch in U.S. Pat. No. 7,175,650.

Alternative mechanical detachment systems for placing an endoluminal implant, while resisting kinking, are described by Hijlkema et al. in U.S. Patent Publication No. 2010/0063573. An outer slidable sheath has an advanced position covering an implant and a retracted position which exposes the implant. In one aspect, at least one of the proximal end of a catheter tip or a stabilizer distal end forms a docking section which releasably engages a portion of the implant when the outer sheath is withdrawn proximally past the docking section. Each docking section has an engagement geometry with a flared engagement surface or a pocket with a bottleneck geometry. In another aspect, an inner tubular member with one or more flexible fingers engages the implant when the sheath is in the advanced position. Again, the outer sheath is retracted to deploy the implant.

Stent-like, generally non-deployable devices are also utilized to treat disorders arising from embolisms and atherosclerosis. An embolism is the sudden obstruction of a blood vessel by blood clots, cholesterol-containing plaques, masses of bacteria and other debris. A blood clot which obstructs a blood vessel is also referred to as a thrombus. If the embolic obstruction occurs in the brain, it can cause a sudden loss of neurological function referred to as a stroke, in particular an acute ischemic stroke.

A number of devices for treating embolic strokes and atherosclerotic deposits are described for example in U.S. Pat. No. 5,972,019 by Engelson et al. Other, more recent neurological devices include the Micrus Revasc™ of Codman & Shurtleff, Inc., the Solitaire™ device of Microtherapeutics, Inc. d/b/a ev3 Neurovascular, and the Trevo™ and Merci Retreiver™ devices from Concentric Medical.

It is therefore desirable to have an improved implant delivery system which retains flexibility during insertion to treat a vascular malformation yet decouples implant release from retraction of a delivery catheter.

SUMMARY OF THE INVENTION

An object of the present invention is to maintain high flexibility in an implant delivery system while controlling implant release independently from retraction of a delivery catheter.

Another object of the present invention is to ensure retractility of the implant after the delivery catheter has been retracted.

This invention features a system for delivering an expandable implant into the vasculature of a patient, including an elongated core element having a proximal end accessible exterior to the patient and a distal end including at least one feature for engaging a proximal portion of the implant in a collapsed state. The system further includes an expansion limiter having an inner diameter and a length sufficient to cover the proximal portion of the implant and to retain the proximal portion in the collapsed state, and at least one elongated member having a distal end connected to the expansion limiter and a proximal end accessible exterior to the patient to enable proximal movement of the expansion limiter to release the implant.

In some embodiments, the system further includes a delivery catheter having an inner diameter sufficiently large to accommodate the core element, the implant in the collapsed state, and the expansion limiter. The engagement feature is a projection from the core element in certain embodiments, and is retractable relative to the core element in other embodiments to assist release of the implant when desired. In some embodiments, the expansion limiter is substantially cylindrical and, in other embodiments, has overlapping edges.

In certain embodiments, the core element is formed of metal and includes a solid wire in proximity to the engagement feature. The member is a filament such as a wire in some embodiments. In other embodiments, the core element and the member are formed from a hypotube, and the engagement feature is retractable into the hypotube in one embodiment.

This invention also features a system for delivering an expandable implant into the vasculature of a patient, including an expandable implant formed of self-expanding material and having a plurality of enlargements, such as radiopaque markers, on at least its proximal portion. The system further includes an elongated core element having a proximal end accessible exterior to the patient and a distal end including a solid core wire defining a recess for receiving the radiopaque markers or other enlargements, and at least one feature for engaging the proximal portion of the implant in a collapsed state. An expansion limiter has an inner diameter and a length sufficient to cover the proximal portion of the implant and to retain the proximal portion in the collapsed state, and the system also includes at least one filament having a distal end connected to the expansion limiter and a proximal end accessible exterior to the patient to enable the expansion limiter to be pulled proximally to release the implant.

BRIEF DESCRIPTION OF THE DRAWINGS

In what follows, preferred embodiments of the invention are explained in more detail with reference to the drawings, in which:

FIG. 1 is a schematic side partial cross-sectional view of the distal portion of a prior art implant delivery system with introducer sheath;

FIG. 2 is a schematic side view of a delivery system according to the present invention;

FIG. 3 is a cross-sectional view of the delivery system of FIG. 2;

FIG. 4 is a cross-sectional view of the core element within the system of FIGS. 2 and 3;

FIG. 4A is an enlargement of a portion A of FIG. 4 showing a solid core wire secured within a hypotube;

FIG. 4B is an enlargement of a portion B of FIG. 4 showing spiral cuts in the hypotube encapsulated by a polymer jacket or sleeve extrusion;

FIG. 5 is a schematic top, partial-cross-sectional view of the proximal portion of an implant captured by a fin-type engagement feature and an expansion limiter according to the present invention;

FIG. 6 is a side view of the complex-geometry expansion limiter of FIGS. 2 and 3;

FIG. 10 is a view similar to that of FIG. 9 after the expansion limiter has been pulled proximally to release the stent for complete deployment;

FIG. 12 is a schematic side view of the distal portion of yet another embodiment according to the present invention having a curved nitinol engagement wire;

FIG. 13 is a partial perspective view of an alternative expansion limiter formed of an overlapping wire mesh in a distal, retention position; and FIG. 14 is a view similar to FIG. 13 with the expansion limiter pulled to a proximal release position.

DETAILED DESCRIPTION OF THE PRESENTLY PREFERRED EMBODIMENTS

Figure 6A:
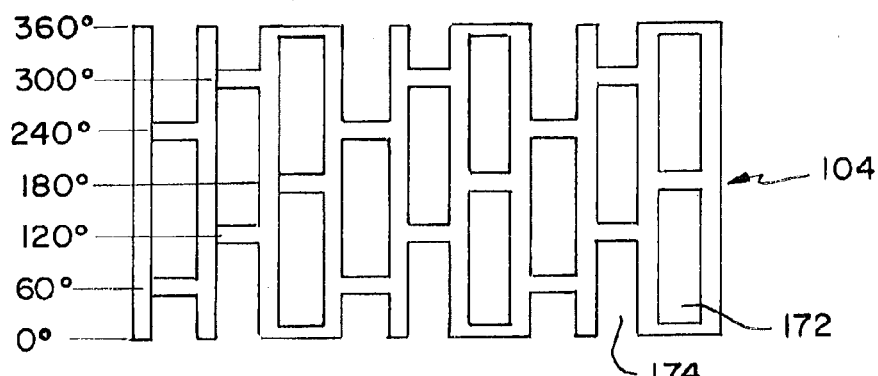
FIG. 6A is an expanded planar view of the expansion limiter of FIG. 6.

This invention may be accomplished by a system for delivering an expandable implant into the vasculature of a patient, where the term "vasculature" is utilized in its broadest meaning to include any duct or tube network in a human or other animal. A delivery system according to the present invention includes an elongated core element having a proximal end accessible exterior to the patient and a distal end including at least one feature for engaging a proximal portion of the implant in a collapsed state. The system further includes an expansion limiter having an inner diameter and a length sufficient to cover the proximal portion of the implant and to retain the proximal portion in the collapsed state, and at least one elongated member having a distal end connected to the expansion limiter and a proximal end accessible exterior to the patient to enable proximal movement of the expansion limiter to release the implant when and if full deployment and detachment are desired.

By comparison, a well-known CODMAN ENTERPRISE® vascular reconstruction device 10 mounted for delivery within a CODMAN ENTERPRISE® vascular reconstruction system 20, both commercially available from Codman & Shurtleff, Inc. as described above, are illustrated schematically in FIG. 1. Device 10 is formed of a self-expanding metal and has a proximal portion 12 and a distal portion 14, each portion carrying four radiopaque markers held within recesses formed in a metallic delivery wire 22 behind a leading distal tip section 24 of wire 22.

Prior art system 20 further includes an introducer sheath 30 formed of a polymeric material and having a tapered distal section 32 terminating in a distal end 34. Tapered distal section 32 mates with a hub at the proximal end of a delivery catheter such as a PROWLER® SELECT® Plus microcatheter as described above. The inner diameter of the delivery catheter is substantially the same as the inner diameter of the introducer 30 so that device 10 is maintained in a collapsed state. However, as soon as the distal end of a catheter containing delivery wire 22 is withdrawn past proximal portion 12, device 10 will fully deploy and separate completely and irretrievably from system 20.

One construction of an improved delivery system 100 according to the present invention is shown in side and cross-sectional views in FIGS. 2 and 3 without an implant and without an outer introducer sheath or delivery catheter, although system 100 preferably is sized to be compatible with device 10 and introducer 30 of FIG. 1 to treat cerebral aneurysms as described above. In describing the present invention, the term "delivery catheter" is utilized in its broadest sense to include any introducer, sheath, catheter, microcatheter, or other elongated device having a lumen through which an elongated core element can be advanced while carrying an expandable implant in a substantially collapsed state.

System 100, FIGS. 2 and 3, includes a core element 102 and an expansion limiter 104 with a distal end 106 and a proximal end 108. Core element 102, also shown in cross-section in FIG. 4, includes a solid core wire distal section 110 having a distal tip 112, a reduced-diameter section 114, an intermediate-diameter section 116, a reduced-diameter section 118, a larger-diameter section 120, an implant engagement feature 122 between reduced-diameter sections 124 and 126, and a proximal end section 128. In this construction, engagement feature 122 has an upper projection 150 and a lower projection 152 which together span nearly the entire inner diameter of expansion limiter 104 along one dimension.

A schematic top, partial cutaway view of a similar system 100a is illustrated in FIG. 5, after a delivery catheter has been withdrawn, with proximal portion 12a of an implant 10a contained by expansion limiter 104a in a recess 126a against a distal core wire 110a of a core element 102a. A fixed, fin-like engagement feature 150a projects radially outwardly through compressed metal struts 162 and may lie against one or more enlargements 160 of implant 10a such as radiopaque wire wrappings. Although the distal portions (not shown) of the implant 10a have expanded and exert distal pulling forces on struts 162 and enlargements 160, at least one engagement feature 150a prevents distal axial movement of implant 10a relative to core element 102a until expansion limiter 104a is pulled proximally.

Core element 102, FIGS. 2-4, further includes a hypotube 130 and a polymer jacket or sleeve 132 in this construction, and solid wire end section 128 has a slightly narrower portion 129, FIG. 4A, which is welded within the distal portion of hypotube 130. As shown in FIG. 4B, an extended section 134 of hypotube 130 has spiral slots 136 fully covered or encapsulated by jacket 132 to enhance overall flexibility of core element 102 while minimizing frictional engagement when core element 102 is advanced or retracted relative to a delivery catheter.

Hypotube 130 of core element 102 defines two slots 140 and 142, FIGS. 2-4, to accept elongated members 144 and 146, respectively, as shown in FIGS. 2 and 3. The distal ends of members 144 and 146 are secured to proximal end 108 of expansion limiter 104, preferably in a symmetrically spaced relationship, while the proximal ends of members 144 and 146 pass through the central lumen of hypotube 130 and preferably extend at least several centimeters beyond the proximal end of hypotube 130, or are otherwise accessible by a user to pull expansion limiter 104 proximally as desired to release an implant as described in more detail below. A trigger, a pull knob, or other actuation mechanism can be connected to members 144 and 146 to exert, when desired, a sufficient pulling force upon expansion limiter 104.

In one construction for treating cerebral aneurysms, distal core wire 110 is formed from a biocompatible material such as nitinol wire having an initial diameter of approximately 0.018 inch to 0.020 inch which is then selectively ground or otherwise machined to form the implant engagement feature 122, having projections 150 and 152 spanning substantially the entire initial wire diameter along a length of approximately 0.02 inch and having a thickness of approximately 0.003 inch, and the various changes in diameter of the core wire described above. The reduced-diameter sections can be as thin as 0.003 inch in diameter. Hypotube 130 is formed of a compatible material, preferably nitinol or other alloy with sufficient kink resistance, having a length of approximately 220 cm and an outer diameter of approximately 0.016 inch. Detachment members 144 and 146 are formed of 0.002 inch diameter wire and are welded at their distal ends to proximal end 108 of expansion limiter 104. Polymer jacket 132 preferably is a low-friction, durable material such as a polyamide.

Expansion limiter 104 is shown in side view in FIG. 6 and in an opened planar view in FIG. 6A with reference points shown for zero degrees through 360 degrees in sixty degree increments to illustrate the various openings cut into limiter 104, such as openings 172 and 174, as one example of a complex geometry which lessens the weight of limiter 104. In one construction for treating cerebral aneurysms with implants that expand to a diameter of approximately 4 mm to 5 mm and have a length of 14 mm to 37 mm (0.55 inch to 1.46 inch), limiter 104 is formed from nitinol to have an overall length LL of approximately 0.112 inch, an outer diameter of 0.020 inch and an inner diameter of 0.018 inch. In other words, length LL of limiter 104 is less than 25 percent of the length of the implant in some constructions, and may be only 10 percent to 20 percent of the overall implant length.

Figure 7:
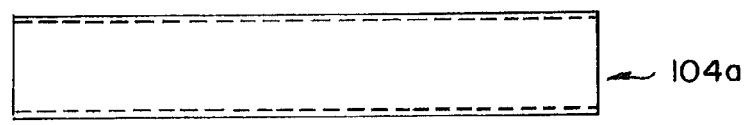
FIG. 7 is a side view of the solid cylindrical expansion limiter of FIG. 5.
Figure 8:
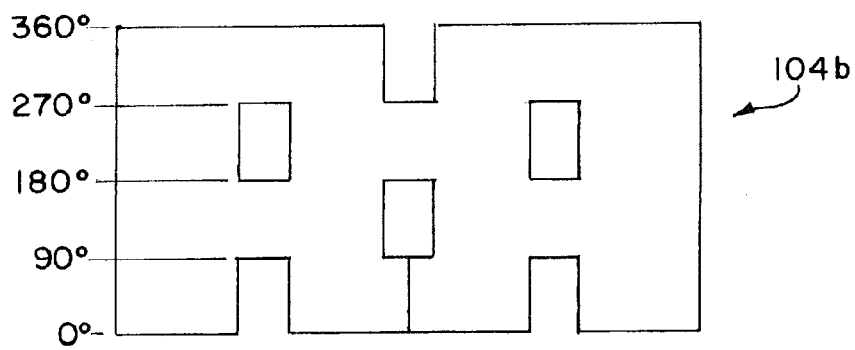
FIG. 8 is an expanded planar view of an intermediate-complexity expansion limiter.

Expansion limiter 104a, FIG. 5, is shown in side view in FIG. 7 as a solid-walled cylinder. Yet another configuration of an expansion limiter 104b is shown in FIG. 8 in expanded planar view with fewer openings or cut-outs.

Figure 9:
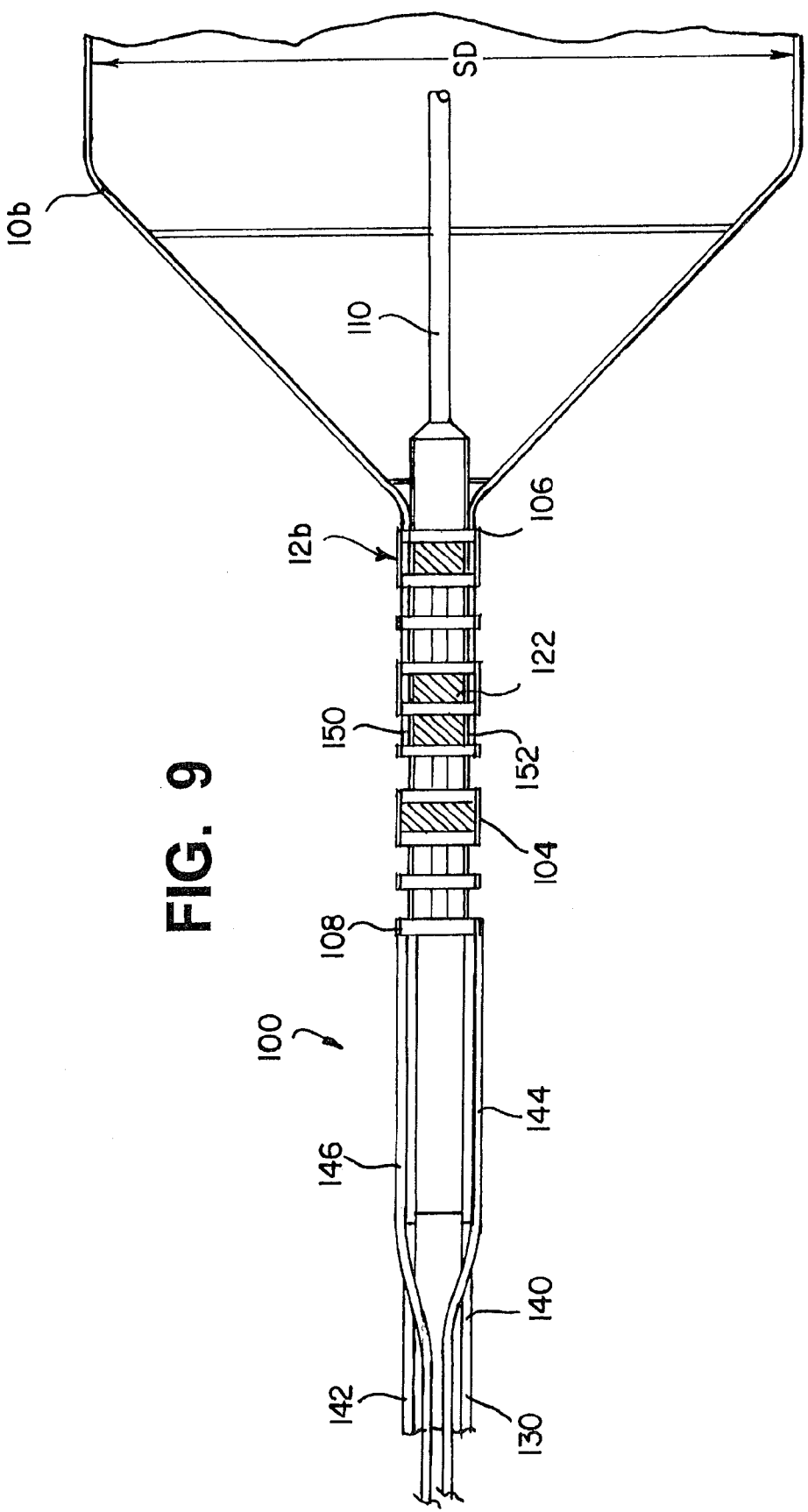
FIG. 9 is a schematic, partial cross-sectional view of the system of FIGS. 2 and 3 retaining the proximal portion of a stent which has otherwise fully expanded for partial deployment.

A distal portion of delivery system 100 is shown in different stages of deploying a stent 10b in FIGS. 9 and 10 after a delivery catheter (not shown in these views) has been withdrawn at least slightly proximal of engagement feature 122. FIG. 9 illustrates proximal portion 12b of stent 10b still captured by expansion limiter 104 and fin-like projections 150 and 152 of engagement feature 122, while the remainder of stent 10b expands distally beyond limiter distal end 106 until rapidly achieving its full stent diameter SD. As often as desired, stent 10b can be fully recaptured by advancing the delivery catheter relative to system 100.

After a surgeon is fully satisfied with the placement of the stent 10b, pulling force is applied to members 140 and 142 to move limiter 104 to the position illustrated in FIG. 10, such that its distal end 106 is now proximal to feature 122. Proximal portion 12b expands radially outwardly such that stent 10b self-expands to its full diameter SD along its entire length. The remainder of system 100 is then withdrawn, leaving stent 10b in its fully deployed position.

Figure 11:
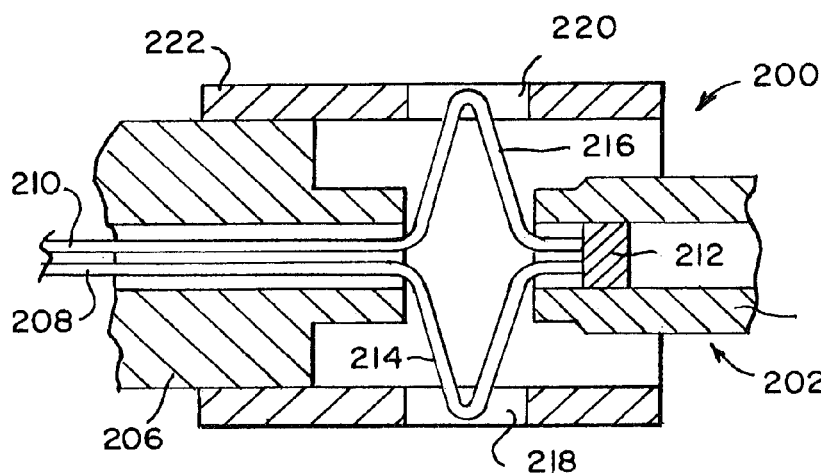
FIG. 11 is a schematic side view of a distal portion of another embodiment of a delivery system according to the present invention having a pair of nitinol wires serving as engagement features.

Delivery system 200, FIG. 11, is an alternative construction according to the present invention. An elongated core element 202 has a distal section 204, formed of a hypotube in this construction, and a proximal delivery section 206, which is also a hypotube and is welded to cylindrical expansion limiter 222 in this construction. Elongated core element 202 further includes a pair of nitinol wires 208 and 210 whose distal ends are secured to distal section 204 by an anchor 212 such as a weld or plug. Wires 208 and 210 include engagement bends 214 and 216 which normally extend into slots 218 and 220, respectively, defined in expansion limiter 222 in this construction. In other constructions, limiter 222 defines one or more annular channels or other types of recesses which are releasably interlockable with bends 214 and 216 and, in yet other constructions, limiter 222 lacks any such interlockable features. However, it is preferable to have a mechanism to couple distal section 204 with proximal section 206 without applying a force to wires 208 and 210 until deployment is desired as described below.

During use of system 200 by a surgeon or other operator to deliver an implant into a blood vessel network or other vasculature, with the proximal portion of the implant being held within limiter 222 and engaged by bends 216 and 218, the operator first positions the system 200 within the vasculature and then withdraws a delivery catheter proximally relative to core element 202 to partially deploy the implant. The implant is then visualized, typically using fluoroscopy, and the implant can be repositioned as often as desired by advancing the delivery catheter to collapse the implant, and then shifting the position of system 200 and withdrawing the delivery catheter again. When the partially deployed implant is in an acceptable position, the operator applies a pulling force to the proximal ends (not shown) of wires 208 and 210 to allow the implant to float freely, and then pulls back slightly on proximal delivery section 206 to release the implant from the expansion limiter 222. The implant becomes fully deployed and system 200 is removed from the patient.

Yet another delivery system 300 according to the present invention, FIG. 12, has a retractable and removable engagement feature 301 having a distal projection 303 which passes through a passage 304 in a reduced-diameter region of an elongated core element 302. In one construction, at least the distal portion 303 of engagement feature 301 is a heat-shaped nitinol wire, and the implant is held solely by distal projection 303 until a pulling force is applied to feature 301 to withdraw distal portion 303 at least through passage 304 and preferably beyond shoulder 308. In another construction, an expansion limiter is added to system 300 to further control the proximal section of an implant until full deployment is desired.

A still further delivery system 400 according to the present invention, FIGS. 13 and 14, includes an expansion limiter 402 formed of a curved sheet of solid or open material, such as a wire mesh, having overlapping side edges. Expansion limiter 402 is positioned relative to a feature 403 on an elongated core element 404 in an implant engagement position as shown in FIG. 13 and in an implant release position as shown in FIG. 14. In this construction, feature 403 is a larger-diameter section of element 404 distal to a reduced-diameter section 405. Proximal enlargements, such as radiopaque markers, on an implant are nestled into reduced-diameter section 405 and held in place by expansion limiter 402 during delivery. An elongated member 406 is attached at its distal end 408 to a proximal edge of limiter 402 to enable limiter 402 to be pulled proximally when full implant deployment is desired.

Physicians may also choose to use a delivery system according to the present invention to treat acute ischemic stroke or other vascular disorder without detaching a stent or other implant-like device. The delivery system may be guided through the vasculature to displace and retrieve a thrombus or other emboli by entangling it in the struts of the expanded implant while the implant remains attached to the delivery system. In one procedure, the delivery system with a fully-collapsed stent is advanced through a thrombus and then the delivery catheter is withdrawn to expand most of the stent, causing the struts of the stent to force themselves into the thrombus. The delivery system is then withdrawn with engaged thrombus.

In circumstances where an embolus or plaque is too adhered to a vessel wall and cannot be removed, a physician may decide to fully deploy and detach the stent to keep the vessel lumen open. Delivery systems according to the present invention increase the options available to a physician by enabling full stent deployment and detachment only when and if desired.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A system for delivering an expandable implant into the vasculature of a patient, comprising:
an elongated core element having a proximal end accessible exterior to the patient and a distal end including at least one feature for engaging a proximal portion of the implant in a collapsed state;
an expansion limiter having an inner diameter and a length sufficient to cover the proximal portion of the implant and to retain the proximal portion in the collapsed state; and
at least one elongated member having a distal end connected to the expansion limiter and a proximal end accessible exterior to the patient to enable proximal movement of the expansion limiter to immediately release and expand the implant.

2. The system of claim 1 further including a delivery catheter having an inner diameter sufficiently large to accommodate the core element, the implant in the collapsed state, and the expansion limiter.

3. The system of claim 1 wherein the feature is a projection from the core element.

4. The system of claim 1 wherein the feature is retractable relative to the core element to assist release of the implant.

5. The system of claim 1 wherein the expansion limiter is substantially cylindrical.

6. The system of claim 1 wherein the expansion limiter has overlapping side edges.

7. The system of claim 1 wherein the core element is formed of metal.

8. The system of claim 1 wherein the core element includes a solid wire in proximity to the feature.

9. The system of claim 1 wherein the member is a filament.

10. The system of claim 9 wherein the filament is a wire.

11. The system of claim 1 wherein the core element and the member are formed from a hypotube.

12. The system of claim 11 wherein the feature is retractable into the hypotube to assist release of the implant.

* * * * *